(12) United States Patent
Tan et al.

(10) Patent No.: US 6,532,063 B1
(45) Date of Patent: Mar. 11, 2003

(54) 3-D LEAD INSPECTION

(75) Inventors: Seow Hoon Tan, Singapore (SG); Sreenivas Rao, Singapore (SG)

(73) Assignee: Semiconductor Technologies & Instruments, Dallas, TX (US)

( * ) Notice: Subject to any disclaimer, the term of this patent is extended or adjusted under 35 U.S.C. 154(b) by 0 days.

(21) Appl. No.: 09/710,448

(22) Filed: Nov. 10, 2000

(51) Int. Cl.⁷ .............................................. G01N 21/00
(52) U.S. Cl. ................................................... 356/237.1
(58) Field of Search ........................... 356/237.1, 240.1, 356/614, 615, 622; 250/559.08, 559.34; 382/145, 146, 147, 148, 149, 150, 151, 260

(56) References Cited

U.S. PATENT DOCUMENTS

| | | | |
|---|---|---|---|
| 4,696,047 A | | 9/1987 | Christian et al. ............... 382/8 |
| 4,872,052 A | | 10/1989 | Liudzius et al. ............. 358/106 |
| 5,131,753 A | * | 7/1992 | Pine et al. .................... 356/375 |
| 5,452,080 A | * | 9/1995 | Tomiya ..................... 356/237.1 |
| 5,457,538 A | * | 10/1995 | Ujie ............................. 356/399 |
| 5,739,525 A | * | 4/1998 | Greve .................... 250/227.11 |
| 5,838,434 A | * | 11/1998 | Skramsted et al. .......... 356/243 |
| 5,956,134 A | | 9/1999 | Roy et al. ................. 356/237.5 |
| 6,005,965 A | * | 12/1999 | Tsuda et al. ................. 382/145 |
| 6,055,055 A | | 4/2000 | Toh .............................. 356/376 |
| 6,088,108 A | | 7/2000 | Toh et al. ..................... 356/375 |

* cited by examiner

Primary Examiner—Michael P. Stafira
(74) Attorney, Agent, or Firm—Baker Botts LLP

(57) ABSTRACT

A semiconductor lead inspection device includes a camera and an illumination source for backlighting the leads of the semiconductor device to form an image in the camera. The camera and the illumination device are arranged on optical paths which alternatively pass through or are reflected by a beamsplitter. A surface is illuminated to backlight the leads and a light deflecting device is arranged for deflecting the backlit image of the semiconductor leads to form an image in the camera.

14 Claims, 4 Drawing Sheets

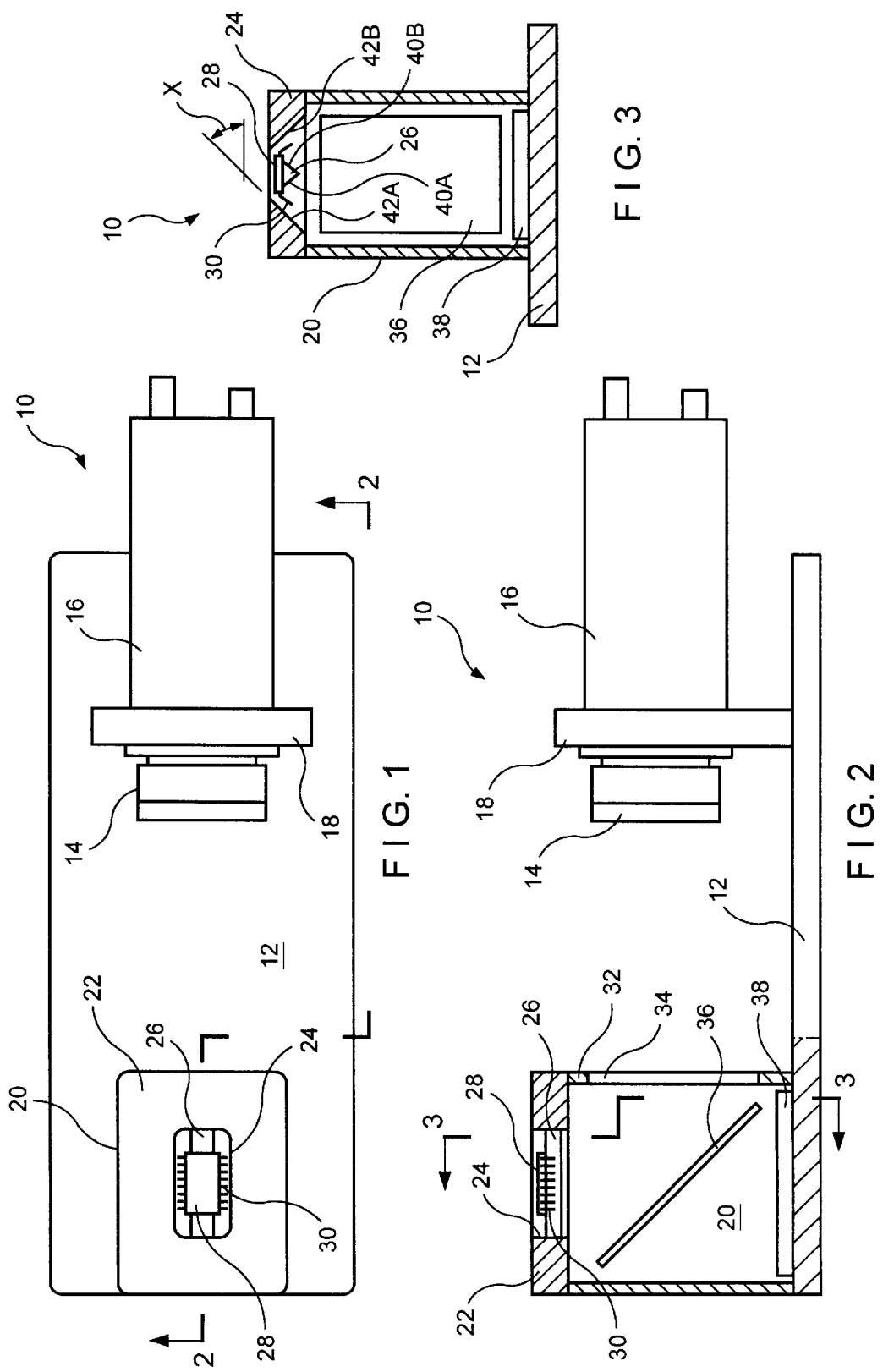

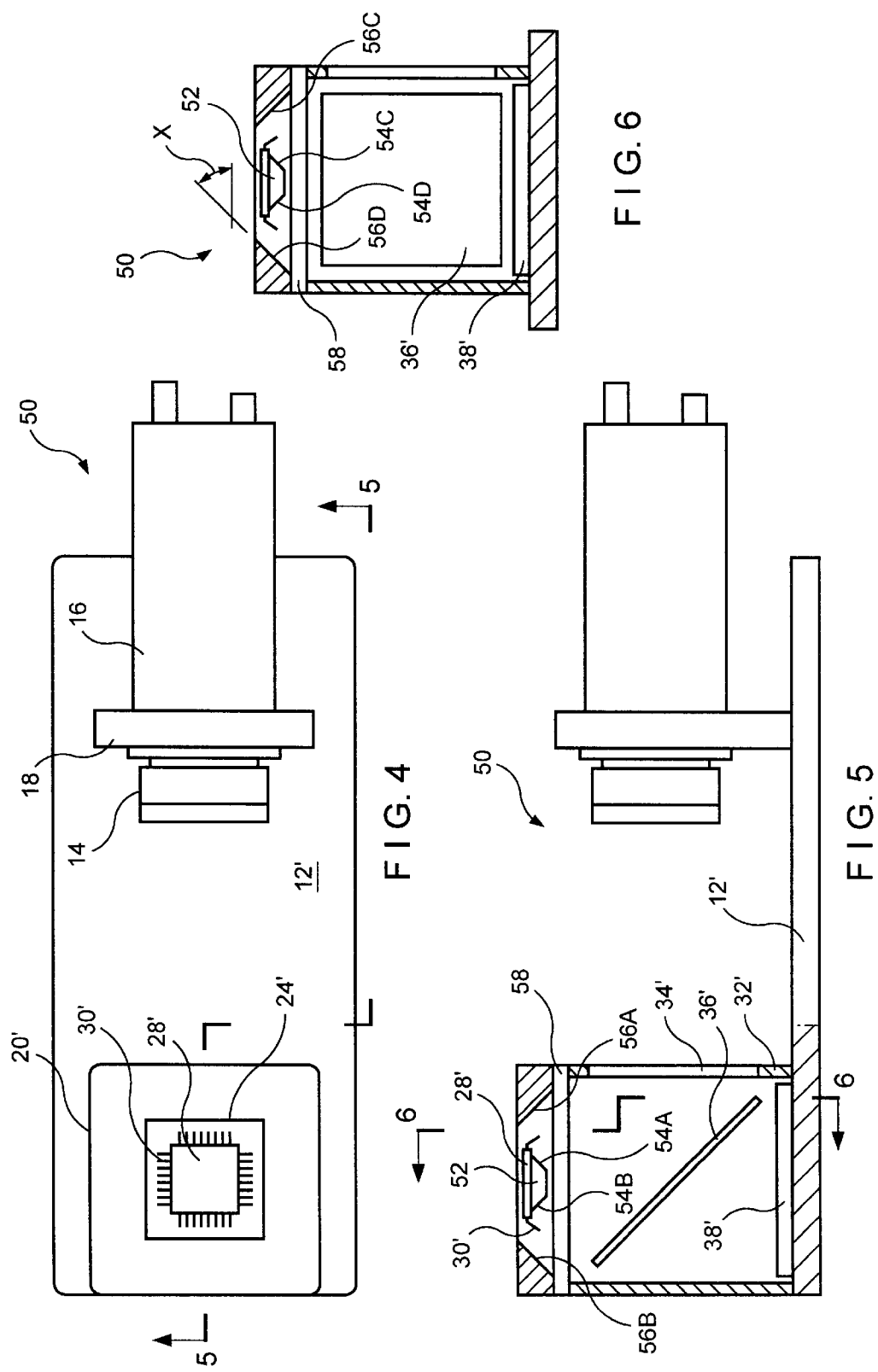

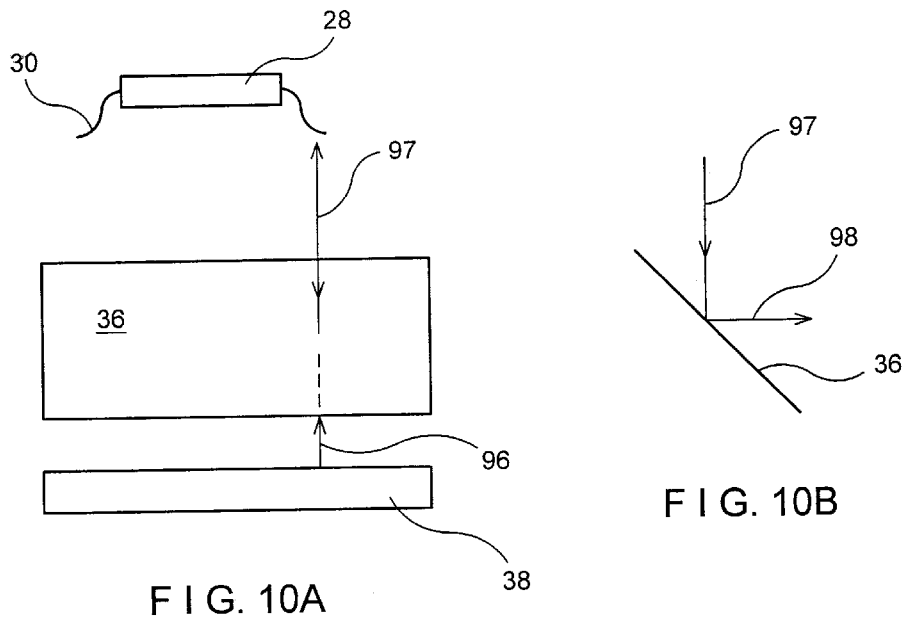
FIG. 10A
FIG. 10B
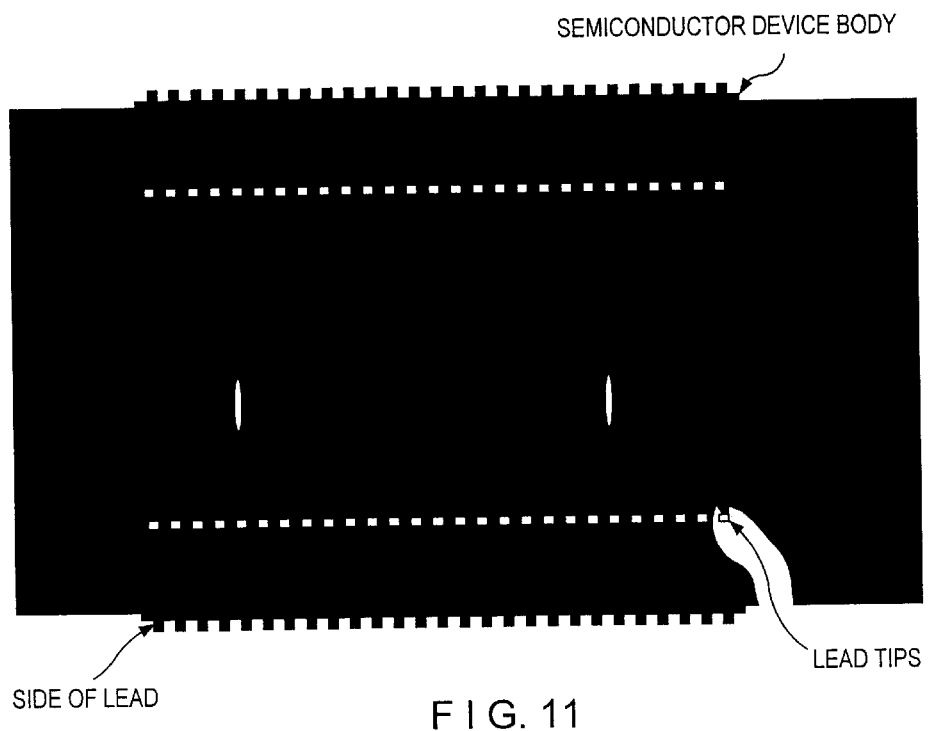
FIG. 11

3-D LEAD INSPECTION

BACKGROUND OF THE INVENTION

This invention relates to an apparatus and method for optical inspection of the leads of semiconductor chip devices. Semiconductor chip devices come in a number of standard sizes and have protruding leads or connector pins which must be inspected during the manufacturing process to assure that the leads are aligned and have the proper end orientation. The requirement of lead inspection is to assure that the semiconductor chip devices have leads which are aligned and oriented to enable automatic insertion of the semiconductor chip device into a circuit board.

Existing lead inspection devices have an illumination system which is arranged above the device inspection station, or on the sides thereof, and an imaging system arranged either below the inspection station, or vice-versa. This arrangement is not easily suitable for use with a system that uses an automated device to pick-up and place semiconductor devices to be inspected at the inspection station of the apparatus. In the prior devices the optical system may interfere with the operation of an automated semiconductor device placement apparatus.

It is an object of the present invention to provide an improved inspection apparatus and method in which substantially all of the optical components, the illumination system and the imaging system, are positioned on only one side of the inspection station. Therefore, three-dimensional inspection of leads can be made with clearance at the top of the inspection station, so that optical inspection can take place using an automated device-handling mechanism.

SUMMARY OF THE INVENTION

In accordance with the invention, there is provided apparatus for optically inspecting connector pins of a semiconductor device. A light source is provided for providing illumination along a first optical path, which includes an optical beam splitter. A camera is arranged to receive light from the optical beam splitter along a second optical path, generally transverse to the first optical path. An inspection station is arranged to receive a semiconductor device. A surface on one side of connector pins of a semiconductor device received at the inspection station is illuminated by light from the light source. The illuminated surface provides backlight illumination of the pins. A backlit image of the pins is deflected by a light deflecting device, and reflected by the beamsplitter onto the second optical path toward the camera.

In a preferred embodiment, the inspection station comprises a horizontal platform for receiving the semiconductor device. In one arrangement for inspecting a semiconductor device having two rows of connector pins, there are provided two of the light deflector devices and two illuminated surfaces In an arrangement for inspecting a semiconductor device having four rows of connector pins, there are provided four of the first light deflecting devices and four of the illuminated surfaces.

According to the invention, the light source and the camera can be interchanged in relation to the beamsplitter.

According to the invention, a method is provided for inspecting connector pins of a semiconductor device by providing back illumination of the connector pins along a first optical path which is reflected by a beamsplitter, directing light passing the connector pins onto a second optical path towards the beamsplitter, and detecting light passing through the beamsplitter to form an image of the connector pins.

In accordance with the invention, there is also provided a method for inspecting connector pins of a semiconductor device wherein back illumination of the device connector pins is provided along a first optical which passes through the beamsplitter, wherein light passing the connection pins is directed along a second optical path toward the beamsplitter and light reflected by the beamsplitter is detected to form an image of the connecting pins.

In a preferred arrangement illumination light from the beamsplitter also directly illuminates the semiconductor pins and is reflected from the pins toward the beamsplitter to form a further image of the pins.

For a better understanding of the present invention, together with other and further objects, reference is made to the following description, taken in conjunction with the accompanying drawings, and its scope will be pointed out in the appended claims.

BRIEF DESCRIPTION OF THE DRAWINGS

FIG. 1 is a top view of a first apparatus in accordance with the present invention.

FIG. 2 is a partial cross-sectional view of the apparatus of FIG. 1.

FIG. 3 is a further cross-sectional view of the apparatus of FIG. 1.

FIG. 4 is a top view of a second embodiment of an inspection device according to the present invention.

FIG. 5 is a partial cross-sectional view of the FIG. 4 device.

FIG. 6 is further cross-sectional view of the FIG. 4 device.

FIG. 10 shows the optical paths for the formation of an additional image portion in the apparatus of FIG. 8.

FIG. 11 is an example of an image provided by the apparatus of FIG. 1.

DESCRIPTION OF PREFERRED EMBODIMENTS

Figure 7:
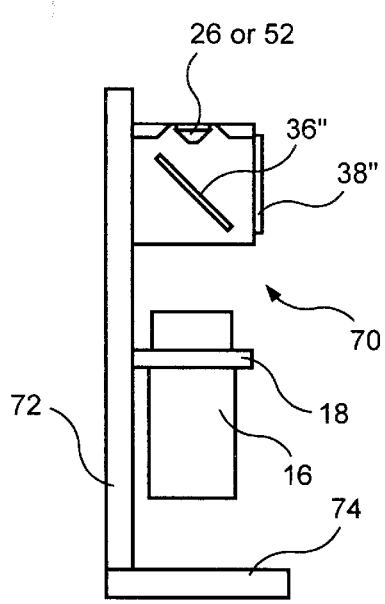
FIG. 7 is a simplified diagram showing a further alternate arrangement of the apparatus of the present invention.

Referring to FIGS. 1 through 3, there is shown a first embodiment of the invention comprising an apparatus 10 for inspecting the leads of a semiconductor device. The apparatus includes a support platform 12, upon which there is mounted a digital camera 16, which may, for example, be a Hitachi Model KP-M1EK for capturing images of the leads of a semiconductor device 28 undergoing optical inspection. Camera 16 includes a lens system 14 and is mounted to support platform 12 by support member 18. An inspection station 20 is also mounted on support platform 12 and includes an opening 24 in an upper wall 22. Within opening 24 there is provided a platform 26 for supporting semiconductor device 28 while it is undergoing inspection. Support platform 26 is narrower than the body of semiconductor device 28, so that the body and leads 30 of device 28 project beyond the edges of platform 26. Referring to the side view of FIG. 2, it can be seen that the leads 30 of semiconductor device 28 project downwardly from the upper surface of platform 26. Inspection station 20 includes an opening 34 in sidewall 32, which enable images of the semiconductor lead to be reflected into camera 16 by beam splitter 36, which may be a half-silvered mirror or other beam splitting device such as dual prisms. A source of illumination 38 is arranged at the bottom of inspection station 20 and provides illumination of the device undergoing inspection by the passage of light through beamsplitter 36. As may be seen in the cross-sectional view of FIG. 3, inspection station 20 includes platform member 26 which has inclined side and lower surfaces 40A and 40B, which are illuminated by source 38 to provide backlight illumination of leads 30 forming a backlit image which is reflected by reflective surfaces 42A and 42B. After reflecting from surfaces 42A and 42B, an image of the backlit ends of leads 30 of device 28 may be formed by camera 16 after having been reflected by beamsplitter 36.

Figure 8A:
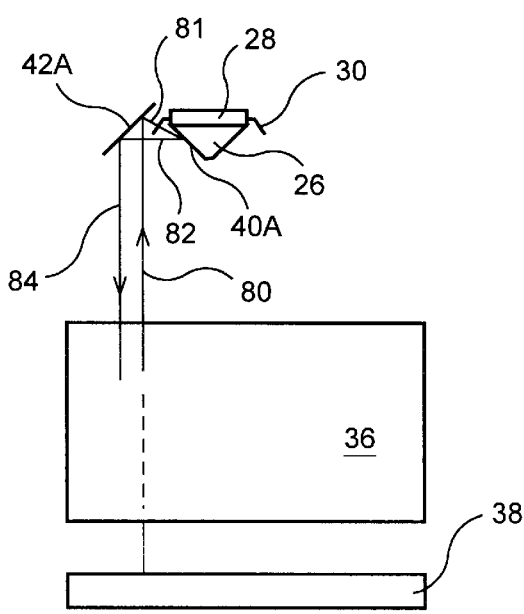
FIG. 8 is a simplified diagram showing the optical paths of the FIG. 1 apparatus.
Figure 8B:
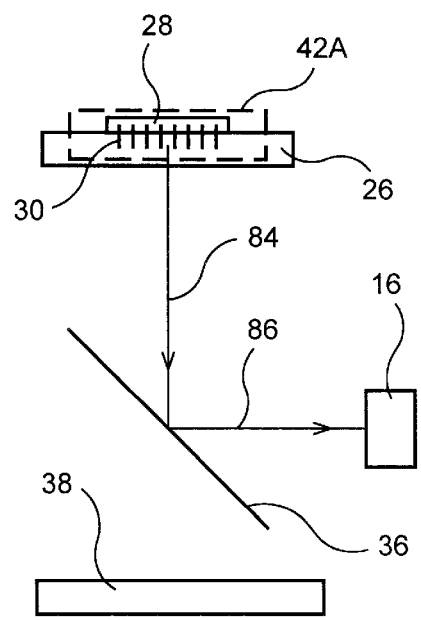

Referring to FIG. 8, there is shown a diagram which indicates the paths of light in connection with the inspection of leads 30 of semiconductor device 28. Illuminating light form source 38 passes along beam path 80 through beamsplitter 36 and is reflected off reflective surface 42A. The reflected illumination follows optical path 81 which illuminates surface 40A, which provides back illumination for the ends of the leads 30. Surface 40A may also be directly illuminated. A backlighted image of leads 30 on optical path 82 is reflected by reflecting device 42A onto optical path 84 which intersects beamsplitter 36 and is reflected on optical path 86, which is generally transverse to path 80, but not necessarily perpendicular thereto, into camera 16. Surfaces 40A may, for example, be a highly polished metal surface of the semiconductor support platform 26, which may, for example, be fabricating from tungsten carbide which has been highly polished. Likewise, mirror 42A may be either a highly polished metal surface or a mirror. Reflecting device 42A is also referred to as a light deflecting device. Other light deflecting devices, such as reflectors or prisms may also be used.

The image captured by camera 16 may be digitized and supplied to a computer for analysis of lead end positions using techniques used in the art.

It will be seen in FIGS. 1 through 3 that the arrangement shown there is for inspecting a semiconductor device 28 that includes leads 30 along two sides. The device shown in FIGS. 4, 5, and 6 is for simultaneous inspection of the leads arranged on four sides of a semiconductor device 28'. Inspection system 50 includes lens 14, camera 16 and support 18, which are similar or identical to those used in connection with device 10 of FIG. 1. The shape of inspection station 20' shown in FIG. 4 is more square in configuration to accommodate a square opening 24' and a square semiconductor chip 28' having leads 30' arranged on four sides thereof. As can be seen from the cross-sectional view of FIG. 5, there is provided a semiconductor device support platform 52, which is mounted onto a transparent support plate 58 and includes four inclined surfaces 54A, 54B, 54C and 54D which are illuminated by light source 38' from mirrors 56A, 56B, 56C, and 56D or directly to provide back illumination of leads 30' on the four sides of semiconductor device 28'. Images are deflected toward beamsplitter 36' by reflecting surfaces 56A, 56B, 56C and 56D.

Those skilled in the art will recognize that the location of the images of the leads 30 or 30' of the semiconductor devices 28 or 28' on the image plane of camera 16 can be adjusted by adjusting the angle X of surfaces 42A, 42B, 56A, 56B, 56C and 56D to position the reflected images around the image plane of camera 16. Normally, surfaces 40 and 54 may be at an angle of 45 degrees to the horizontal as shown in FIGS. 2 and 5 and surfaces 42 and 56 may be adjusted depending on the desired image location from an angle X of about 40 degrees to about 50 degrees from the horizontal as shown in FIGS. 3, 6 and 9.

FIG. 7 is a simplified diagram of an alternate arrangement of an inspection apparatus 70 according to the invention. Apparatus 70 includes a horizontal support structure 74 and a vertical support structure 72 upon which the inspection station and camera are mounted. The illumination source 38" is arranged to the right of the beamsplitter 36" so that the illumination light is reflected by beamsplitter 36". Camera 16 is located below beamsplitter 36" such that it receives light that passes through beamsplitter 36". The semiconductor device mounting platform 52 or 26 is mounted at the top. Alternately, the device can have a different orientation from that illustrated. It is also possible to provide additional optical devices, such as reflectors, to relay images to camera 16 at a more convenient location.

Figure 9:
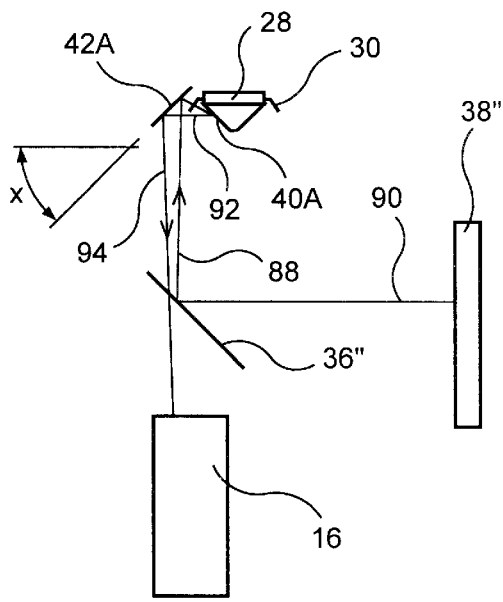
FIG. 9 is a simplified diagram showing the optical paths of the apparatus of FIG. 7.

The operation of the FIG. 7 apparatus 70 is illustrated by the optical path diagram of FIG. 9, wherein light emerges from light source 38" along beam path 90 and is reflected in beamsplitter 36" to optical path 88. Reflecting device 42A deflects the illumination light to illuminate surface 40A and provide backlight illumination of the ends of the leads 30 of the semiconductor device. The backlit image of the leads is reflected by surface 42A having a selected angle X from horizontal onto beam path 94 which passes through beamsplitter 36" to camera 16.

Reflector 42 preferably has an angle X of about 40° so that the backlit image of the leads is formed toward the edge of the image plane. A direct image of the lead ends can also be formed by direct illumination thereof from the light source along beam path 96, as shown in FIG. 10. The reflected image of lead ends along path 97 is reflected along beam path 98 to the camera.

FIG. 11 shows an image of the semiconductor device formed by the camera. In a preferred arrangement support 26 is smaller than the body of device 28, so that the edge of the semiconductor device body appears at the edge of the image along with the backlit image of the side of the leads, as indicated in FIG. 11. The front illuminated lead tips form a direct image toward the image center as shown in FIG. 11.

While there have been described what are believe to be the preferred embodiment of the present inventions, those skilled in the art will recognize that other and further modifications may be made thereto without departing from the spirit of the invention and it is intended to claim all such changes and modifications that fall within the true scope of the invention.

We claim:

1. Apparatus for optically inspecting connector pins of a semiconductor device, comprising:

a light source for providing illumination along a first optical path;

an optical beamsplitter in said first optical path;

a camera arranged to receive light from said beamsplitter along a second optical path generally transverse from said first optical path;

an inspection station arranged to receive a semiconductor device;

a surface for receiving illumination from said light source and arranged on one side of pins of a semiconductor device at said inspection station; and at least one light deflecting device on the other side of said pins from said surface for directing a backlight image of said pins toward said beamsplitter to cause said beamsplitter to direct said light to said camera along said second optical path.

2. Apparatus as specified in claim 1 wherein said inspection station comprises a horizontal platform for receiving said semiconductor device and wherein said surface comprises an angled reflecting surface arranged below said horizontal platform.

3. Apparatus as specified in claim 2 wherein said light deflecting devices comprises a mirror.

4. Apparatus as specified in claim 1 for inspecting a semiconductor device having two rows of connector pins and including two of said surfaces to backlight said two rows of connector pins and two of said deflecting devices for deflecting light toward said beamsplitter.

5. Apparatus as specified in claim 1 for inspecting a semiconductor device having four rows of connector pins and including four of said surfaces to backlight said four rows of connector pins and four of said light deflecting devices for deflecting light toward said beamsplitter.

6. Apparatus for optically inspecting connector pins of a semiconductor device comprising:

a light source for providing illumination along a first optical path;

a beamsplitter arranged for deflecting illuminating light from said first optical path to a second optical path generally transverse to said first optical path;

a camera arranged to receive light passing through said beamsplitter along a third optical path generally transverse to said first optical path;

an inspection station arranged to receive a semiconductor device;

at least one surface for receiving illumination from said light source and arranged on one side of connector pins of a semiconductor device received at said inspection station; and at least one light deflecting device on the other side of said pins from said surface for directing a backlight image of said pins toward said beamsplitter.

7. Apparatus as specified in claim 6 wherein said inspection station comprises a horizontal platform for receiving said semiconductor device and wherein said surface comprises an angled reflecting surface arranged below said horizontal platform.

8. Apparatus as specified in claim 7 wherein said second light deflecting devices comprises a mirror.

9. Apparatus as specified in claim 6 for inspecting a semiconductor device having two rows of connector pins and including two of said surfaces to backlight said two rows of connector pins and two of said light deflecting devices for deflecting light toward said beamsplitter.

10. Apparatus as specified in claim 6 for inspecting a semiconductor device having four rows of connector pins and including four of said surfaces to backlight said four rows of connector pins and four of said light deflecting devices for deflecting light toward said beamsplitter.

11. A method for inspecting connector pins of a semiconductor device, comprising:

providing backlight illumination of said connector pins via a first optical path which is reflected by a beamsplitter;

directing light passing said connector pins onto a second optical path toward said beamsplitter; and detecting light passing through said beamsplitter to form an image of said connector pins.

12. A method as specified in claim 11 further including illuminating ends of said connector pins via said first optical path and detecting light reflected by said pins and passing through said beamsplitter.

13. A method for inspecting connector pins of a semiconductor device, comprising:

providing backlight illumination of said connector pins via a first optical path which passes through a beamsplitter;

directing light passing said connector pins onto a second optical path toward said beamsplitter; and detecting light reflected by said beamsplitter to form an image of said connector pins.

14. A method as specified in claim 13 further including illuminating ends of said connector pins via said first optical path and detecting light reflected by said pins and reflected by said beamsplitter.

* * * * *